United States Patent
Newell

(10) Patent No.: US 11,747,043 B2
(45) Date of Patent: Sep. 5, 2023

(54) FLUID HEATING APPARATUSES, SYSTEMS, AND METHODS

(71) Applicant: NxStage Medical, Inc., Lawrence, MA (US)

(72) Inventor: Scott W. Newell, Ipswich, MA (US)

(73) Assignee: NxStage Medical, Inc., Lawrence, MA (US)

(*) Notice: Subject to any disclaimer, the term of this patent is extended or adjusted under 35 U.S.C. 154(b) by 537 days.

(21) Appl. No.: 16/884,092

(22) Filed: May 27, 2020

(65) Prior Publication Data

US 2020/0284471 A1    Sep. 10, 2020

Related U.S. Application Data

(60) Division of application No. 15/869,656, filed on Jan. 12, 2018, now Pat. No. 10,697,667, which is a
(Continued)

(51) Int. Cl.
| | |
|---|---|
| *F24H 1/12* | (2022.01) |
| *F24H 1/14* | (2022.01) |
| *A61M 5/44* | (2006.01) |
| *H05B 3/26* | (2006.01) |
| *F24H 9/20* | (2022.01) |
| *A61M 1/34* | (2006.01) |

(52) U.S. Cl.
CPC ............ *F24H 1/121* (2013.01); *A61M 5/44* (2013.01); *A61M 5/445* (2013.01); *F24H 1/142* (2013.01); *F24H 9/2028* (2013.01); *H05B 3/262* (2013.01); *A61M 1/342* (2013.01)

(58) Field of Classification Search
None
See application file for complete search history.

(56) References Cited

U.S. PATENT DOCUMENTS 3,485,245 A * 12/1969 Terwilliger ........ G05D 23/1906
                                                    392/479
3,891,827 A    6/1975 Wyse
(Continued)

FOREIGN PATENT DOCUMENTS

| CN | 201537296 U | 8/2010 |
|---|---|---|
| EP | 2009365 A1 | 12/2008 |

OTHER PUBLICATIONS

Banerjee et al., "Antifouling Coatings: Recent Developments in the Design of Surfaces That Prevent Fouling by Proteins, Bacteria, and Marine Organisms", Advanced Materials, 2011, pp. 690-718, Published Sep. 30, 2010.
(Continued)

*Primary Examiner* — John J Norton
(74) *Attorney, Agent, or Firm* — Potomac Law Group, PLLC

(57) ABSTRACT

A low leakage current fluid heater and systems and methods thereof. The fluid heater has a configuration whereby a heating element is isolated from a fluid channel so as to leak into fluid passing through the channel an allowed amount of leakage current. Fluid passing through the fluid heater can be heated to a desired temperature. A controller can provide control signals to driver the fluid heater to the desired temperature and maintain the temperature at the desired temperature.

14 Claims, 17 Drawing Sheets

Related U.S. Application Data continuation of application No. 14/115,807, filed as application No. PCT/US2012/037854 on May 14, 2012, now abandoned.

(60) Provisional application No. 61/485,340, filed on May 12, 2011.

(56) References Cited

U.S. PATENT DOCUMENTS

| | | | |
|---|---|---|---|
| 4,041,276 A | 8/1977 | Schwarz et al. | |
| 4,155,852 A | 5/1979 | Fischel et al. | |
| 4,483,341 A | 11/1984 | Witteles | |
| 4,532,414 A * | 7/1985 | Shah | A61M 5/44 219/535 |
| 4,574,876 A * | 3/1986 | Aid | A61M 1/166 165/917 |
| 4,772,778 A * | 9/1988 | Ogawa | A61M 5/44 392/480 |
| 4,920,475 A | 4/1990 | Rippel | |
| 5,245,693 A * | 9/1993 | Ford | H05B 3/36 165/169 |
| 5,256,285 A * | 10/1993 | Tomita | B01D 27/08 210/453 |
| 5,381,510 A * | 1/1995 | Ford | H05B 3/36 165/169 |
| 6,146,359 A * | 11/2000 | Carr | A61B 18/18 604/114 |
| 6,175,688 B1 * | 1/2001 | Cassidy | A61M 5/365 604/113 |
| 6,271,506 B1 | 8/2001 | Glaser | |
| 6,421,501 B2 | 7/2002 | Berthou et al. | |
| 6,504,226 B1 | 1/2003 | Bryant | |
| 6,539,172 B2 * | 3/2003 | Akahane | F24H 1/121 604/6.13 |
| 6,746,439 B2 | 6/2004 | Lenker | |
| 7,323,851 B2 | 1/2008 | Markowski | |
| 7,419,597 B2 | 9/2008 | Brugger et al. | |
| 7,780,619 B2 | 8/2010 | Brugger et al. | |
| 2002/0081109 A1 * | 6/2002 | Mitsunaga | A61M 5/44 392/484 |
| 2005/0008354 A1 | 1/2005 | Cassidy | |
| 2006/0122552 A1 | 6/2006 | O'Mahony | |
| 2006/0154357 A1 * | 7/2006 | Hassanein | A01N 1/02 435/284.1 |
| 2007/0142773 A1 | 6/2007 | Rosiello et al. | |
| 2008/0021377 A1 | 1/2008 | Kienman et al. | |
| 2009/0221948 A1 | 9/2009 | Szamostalvi et al. | |
| 2009/0269044 A1 * | 10/2009 | Yamakawa | F24H 9/1827 219/553 |
| 2011/0307117 A1 | 12/2011 | McKinnon et al. | |
| 2013/0259458 A1 | 10/2013 | Beisser et al. | |
| 2013/0267930 A1 | 10/2013 | Robson et al. | |
| 2015/0041398 A1 | 2/2015 | Rijn et al. | |

OTHER PUBLICATIONS

EDN Network, "Design Ideas—Readers Solve Design Problems," Apr. 19, 2012, pp. 46-48 and 50-51.

Examination Report dated Jan. 10, 2014, in GB Patent Application No. 1320724.6.

Examination Report dated Jul. 31, 2014, in Great Britain (GB) Application No. 1320724.6.

International Search Report and Written Opinion for International Application No. PCT/US12/37854, dated Oct. 26, 2012.

Reddy et al., "Silicon Field Effect Transistors as Dual-Use Sensor-Heater Hybrids," Analytical Chemistry, Feb. 2011, 83(3): pp. 888-895.

* cited by examiner

FLUID HEATING APPARATUSES, SYSTEMS, AND METHODS

This application is a divisional of U.S. application Ser. No. 15/869,656 filed on Jan. 12, 2018, which is a continuation of U.S. application Ser. No. 14/115,807 filed on Nov. 5, 2013, which is a national stage entry of International Application No. PCT/US2012/037854, filed on May 14, 2012, which claims the benefit of U.S. Provisional Application No. 61/485,340, filed on May 12, 2011. The entire contents of each of the above applications is expressly incorporated by references herein.

FIELD

The disclosed subject matter involves medical electrical (ME) equipment in the form of fluid heating or warming apparatuses and systems and methods thereof.

BACKGROUND

Prevention and protection against electrical shock or leakage currents is a significant consideration in the design of medical electrical equipment. Leakage currents for medical electrical equipment may be defined by the path current takes and can include earth leakage current, enclosure leakage current (or touch current), patient leakage current, patient auxiliary leakage current, and mains voltage to applied part leakage current.

Most medical electrical equipment or devices have contact with a device operator, a patient, or both. Though leakage currents typically are small, the amount of current required to produce adverse physiological effects on a human body is also small, so such leakage currents must be limited to safe values by the design of medical electrical equipment. Accordingly, medical electrical devices must be designed to pass certain tests to ensure that excessive leakage current does not dissipate from the mains, the device enclosure, or applied parts to and through a human body. Portions of Standard ANSI/AAMI/IEC 60601, for instance, address safety requirements for medical electrical equipment.

Medical electrical equipment has a designated class and type, with categorization into class being based on the form of protection used against electrical shock or leakage current and type designation being defined by the degree of protection from electrical shock or leakage current.

Class I medical electrical equipment has a protective earth connection. The primary means of protection for Class I medical electrical equipment is the insulation between "live" parts and exposed conductive parts, such as a metallic enclosure. Supplemental protection is provided by the protective earth connection. Fault or leakage current can flow from the mains to earth via the protective earth conductive connection, which causes a protective device (e.g., a circuit breaker or a fuse) to disconnect the medical electrical equipment from the supply. Note, of course, that not all medical electrical equipment having a protective earth connection necessarily is classified as Class I medical electrical equipment.

Class II medical electrical equipment, on the other hand, does not have a protective earth, and protection against electrical shock is provided by reinforced insulation or double insulation. For double insulation, primary protection is provided by a first layer of insulation (including air) and secondary protection is provided by a second insulation layer. Leakage current can flow from Class II medical electrical equipment.

Different types of medical electrical equipment include B, BF, and CF and each type can afford a different degree of protection against electrical shock or leakage current. Generally speaking, B is for medical electrical equipment providing a particular degree of protection against electrical shock, particularly regarding allowable leakage currents and reliability of the protective earth connection (if present). BF is as type B, but with isolated or floating (F-type) applied part or parts. CF provides a higher degree of protection against electrical shock than BF, particularly with regard to allowable leakage currents and has floating applied parts. For instance, a Class II CF type medical electrical equipment applied part may be required to be designed to allow leakage current of less than 10 µA. Incidentally, an applied part may be defined as a part of the medical electrical equipment which in normal use necessarily comes into physical contact with the patient for the equipment to perform its function or can be brought into contact with the patient or needs to be touched by the patient.

Leakage current can result due to capacitance between the AC supply and the patient. A low dielectric constant, low surface area, and large spacing are common design requirements for minimizing the flow of leakage current.

SUMMARY

The Summary describes and identifies features of some embodiments. It is presented as a convenient summary of some embodiments, but not all. Further the Summary does not necessarily identify critical or essential features of the embodiments, inventions, or claims.

Fluid heaters or warmers and systems and methods thereof according to embodiments can be used with intravenous (IV) therapies including blood transfusions (e.g., blood normal electrolyte) and fluid infusions (e.g., saline, electrolyte solutions, medicines, specialty pharmaceuticals, lethal injections, etc.).

Included among embodiments described herein are groundless, extracorporeal, in-line fluid heating or warming apparatuses (and systems and methods thereof) characterized by substantially no leakage current or low leakage current, for instance to satisfy existing, contemplated, or future medical standard(s) for acceptable leakage current. Thus, fluid heating apparatuses according to embodiments of the disclosed subject matter either do not substantially induce or otherwise leak current into the fluid flowing through the fluid heater, or only leak or induce an acceptable amount of current into the fluid flowing through the fluid heater. Accordingly, substantially no or an acceptable amount of current may reach a patient intravenously connected to the fluid path heated by a fluid heater according to embodiments of the disclosed subject matter.

In addition to having low or substantially no leakage current, embodiments of the disclosed subject matter can quickly and evenly heat or warm a fluid flowing therethrough at acceptable or optimal application-specific flow rates (e.g., transfusion and infusion flow rates). Real-time temperature sensing also may be implemented for adjusting temperature and/or to monitor fluid or heater temperature against predetermined maximum and minimum temperature values. Optionally the maximum and minimum temperature values may be electronically set or reset by an operator of the fluid heating apparatus.

Fluid heating apparatuses according to embodiments described herein each can be configured as a standalone device, with its own control system, to be used with any suitable fluid processing system. Or, fluid heating apparatuses according to embodiments can be a component of a specific fluid processing system, such as a dialysis machine or system. In the latter case, the fluid heating apparatus may not have its own control system and can thereby be controlled by a controller of the specific fluid processing system, or, a controller of the specific fluid processing system can operate in a master-slave relationship with a controller of the fluid heating apparatus.

According to embodiments, the disclosed subject matter includes any systems and/or methods configured to implement any of the apparatuses described herein.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Any values dimensions illustrated in the accompanying graphs and figures are for illustration purposes only and may not represent actual or preferred values or dimensions. Where applicable, some features may not be illustrated to assist in the description of underlying features.

DETAILED DESCRIPTION

Figure 1A:
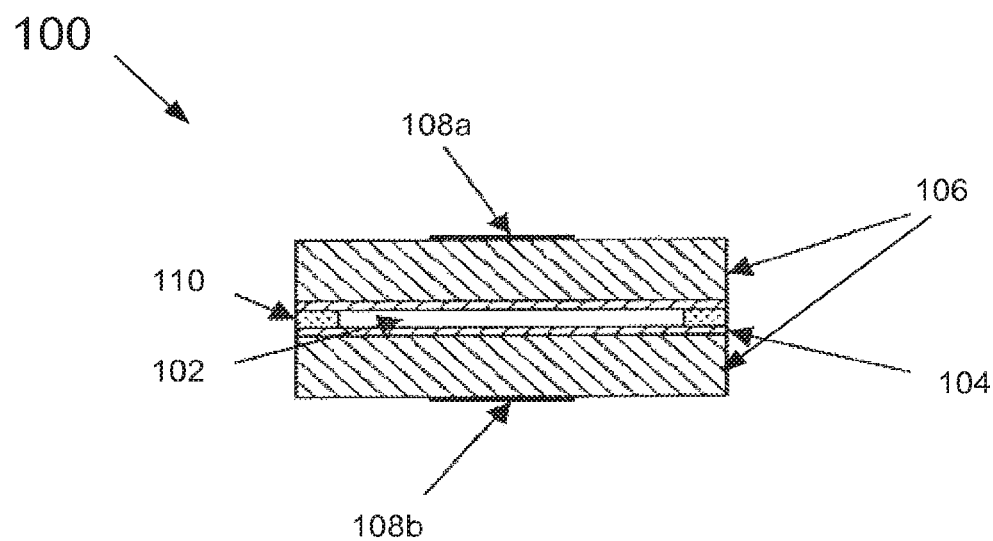
FIG. 1A illustrates a cross-sectional rear view of a fluid heating apparatus according to an embodiment of the disclosed subject matter.

The detailed description set forth below in connection with the appended drawings is intended as a description of various embodiments of the disclosed subject matter and is not intended to represent the only embodiments in which the disclosed subject matter may be practiced. The detailed description includes specific details for the purpose of providing a thorough understanding of the disclosed subject matter. However, it will be apparent to those skilled in the art that the disclosed subject matter may be practiced without these specific details. In some instances, well-known structures and components are shown in block diagram form in order to avoid obscuring the concepts of the disclosed subject matter.

Included among embodiments described herein are fluid heating or warming apparatuses (and systems and methods thereof) characterized by substantially no leakage current or low leakage current, while at the same time sufficiently heating a fluid flowing therethrough to a desired temperature at a given flow rate. Generally speaking, the configuration of fluid heating apparatuses according to embodiments of the disclosed subject matter can have a structure and be operative to provide for heat from one or more heating elements to be distributed to a relatively large surface area for heat transfer to a fluid flowing through a fluid channel or channels of the fluid heating apparatus. Additionally, embodiments of the invention can also include heating elements for heating bags, for instance, providing heat to a relatively large plate or plates.

The fluid can be heated from an initial temperature to a predetermined temperature or temperature range. Moreover, the heat output from the heating element(s) can be maintained so as to uniformly heat fluid flowing through a fluid channel of the fluid heating apparatus. For instance, fluid heating apparatuses according to embodiments of the disclosed subject matter can heat a fluid from 15° C. to 40° C. flowing at a flow rate of 300 ml/min and providing leakage current of less than 10 µA. As another example, fluid can be heated to about 38° C. through about 43° C. at a flow rate of up to 500 ml/min. Heating to the aforementioned temperatures or temperature ranges is not intended to limit the temperature or temperature ranges to which fluid(s) can be heated according to embodiments of the invention. For example, temperatures much higher than the foregoing temperatures or temperature ranges can be achieved, for example, temperatures above the boiling point of water. Fluid temperature can be maintained at any of the aforementioned temperatures or temperature ranges. Additionally, the desired maximum temperature can be set to the aforementioned temperature, the aforementioned temperature range, or a specific temperature in the temperature range. Embodiments of the disclosed subject matter also can warm a product (e.g., blood) from 10° C. at flow rates from 10 to 300 ml/min to a temperature in the range of 35° C. to 40° C. Fluids having flow rates of over 500 ml/min can also be heated. Moreover, heating to temperatures or temperature ranges above 43° C. also can be attained. Higher pressures and bubbles can also be accommodated for or otherwise heated and handled.

Figure 1B:
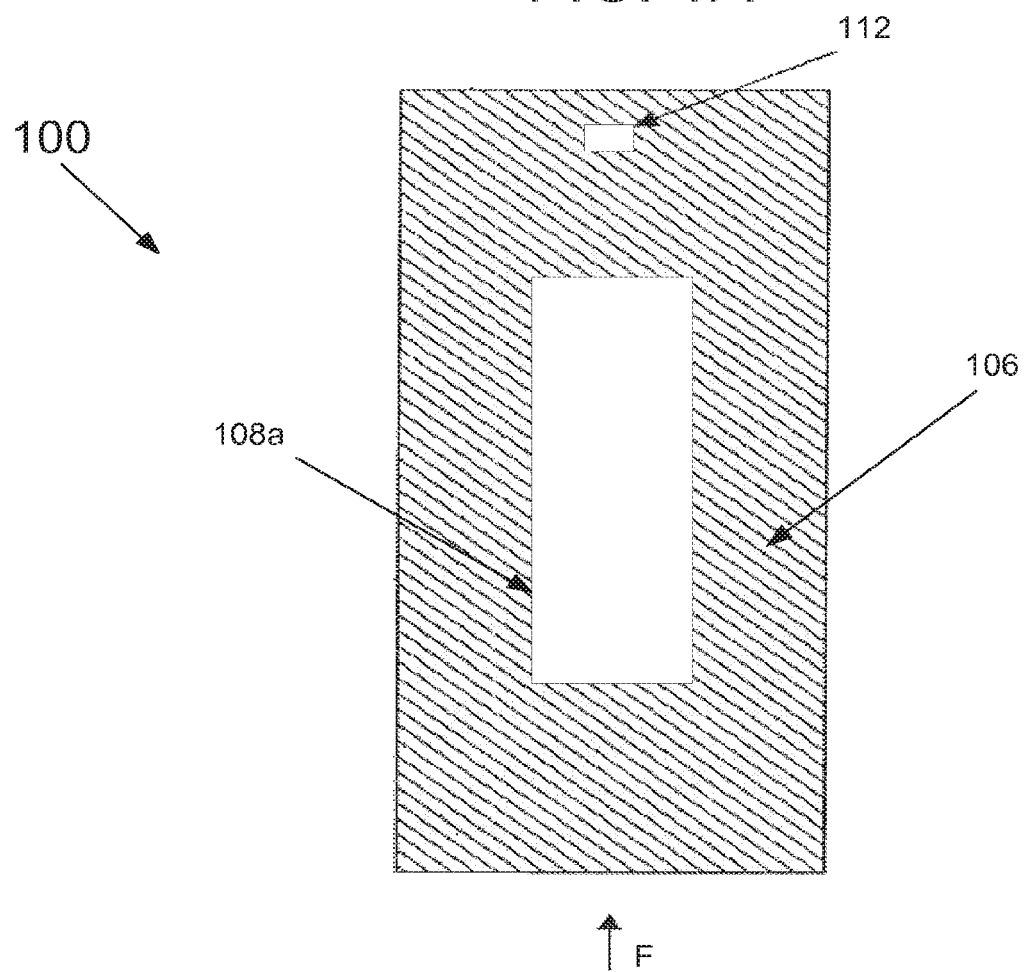
FIG. 1B illustrates an overhead view of the fluid heating apparatus of FIG. 1A.

FIGS. 1A and 1B show a fluid heating apparatus 100 according to embodiments of the disclosed subject matter. Fluid flow direction is into the page for FIG. 1A and upward in FIG. 1B, as indicated by the up-going arrow F.

Fluid heating apparatus 100 includes a fluid channel 102, a fluid channel interface 104 partially surrounding the fluid channel 102, heat spreaders 106 adjacent the fluid channel interface 104, a first heating element 108a, a second heating element 108b, and a seal 110. Fluid heating apparatus 100 also can include a temperature sensor 112. Not shown in FIGS. 1A and 1B, and as will be discussed later, fluid heating apparatus 100 can be electrically coupled to a controller, and the controller can receive feedback signals from temperature sensor 112 and provide control signals to a driver to control operation of the fluid heating apparatus 100, for example, to control operation of the heating element(s), such as on/off operation, the amount of heat output by the heating element(s), ramp up heating time, etc.

Fluid channel 102 generally may be narrow to maximize velocity and minimize volume throughput of a fluid flowing through the fluid channel. In the embodiment shown in FIGS. 1A and 1B, the fluid channel 102 may be formed by fluid channel interface 104 and seal 110. Not explicitly shown, optionally, the fluid channel 102 can be sized as shown in FIG. 1A for the entire length of the fluid heating apparatus 100, or, alternatively, it can be sized as shown in FIG. 1A for only a portion of the length of the fluid heating channel (e.g., only at the middle, only the ends, or only one end of the fluid heating apparatus). Thus, in various embodiments, fluid channel 102 may be of a same size and shape through the length of the fluid heating apparatus 100, and in alternative embodiments the fluid channel 102 can vary in size and shape along the length of the fluid heating apparatus 100.

Both fluid channel interface 104 and seal 110 can be non-fouling, as these components will be in contact with fluids that are to enter a patient, for example. Non-fouling characteristics of the fluid channel interface 104 and the seal 110 can also prolong the life of the fluid channel 102 or the fluid heating apparatus itself and/or it may make the fluid heating apparatus 100 easier to clean. For instance, the fluid channel interface 104 may be a copper plate having a surface treatment thereon, such as a nickel and gold multi-layer plate, film, or laminate. Fluid channel interface 104 and seal 110 can be sealingly coupled together by any suitable means, such as an adhesive, fusing, etc.

Incidentally, optionally, fluid heating apparatuses (including fluid heating apparatus 100) according to embodiments of the disclosed subject matter can have a fluid channel that is configured for bidirectional fluid flow. Alternatively, fluid heating apparatuses according to embodiments of the disclosed subject matter may have a fluid channel configured for unidirectional fluid flow. Thus, in the latter case, indicia, such as positioning of temperature sensor 120 and/or markings may indicate direction of flow and thus instruct an operator or technician, for instance, as to proper orientation for connecting the fluid heating apparatus to attachments, such as fluid flow lines into and out of the fluid heating apparatus.

In various embodiments, the fluid channel interface 104 may be a "stainless" material, such as stainless steel or glass. Alternatively, as discussed above, the fluid channel interface 104 can be a copper plate. Optionally, the inner portion of the copper plate that would otherwise contact the fluid can have a surface treatment thereon. For example, the surface treatment may be an anti-corrosion treatment. Optionally, the surface treatment may be a multi-layer film, plate, or laminate comprised of nickel and gold, with the gold layer forming the fluid contacting surface of the fluid channel interface. Alternatively or optionally, the surface treatment can be a metal vapor deposition.

The seal 110 can be made of any suitable material, in various embodiments of a material different from the fluid channel interface 104, and can create a liquid and/or air-tight seal with the fluid channel interface 104, thereby creating a liquid and/or air-tight fluid channel 102. The seal 110 also can be made of copper, for instance, with a multi-layer film or laminate comprised of nickel and gold, for instance.

On top and bottom of the fluid channel interface 104 are heat spreaders 106, and coupled to the heat spreaders 106 are a plurality of heating elements (the embodiment shown in FIGS. 1A and 1B includes two heating elements 108a, 108b). In various embodiments, heat spreaders 106 may be metallic, for example, aluminum. Heat spreaders 106 can have a relatively large surface area for heat transfer from heating elements 108a, 108b to a fluid flowing through the fluid channel 102.

First and second heating elements 108a, 108b can be of any suitable material and can be comprised of a shell, a heat producing element (not explicitly shown), and electrical connections or terminals (not shown) to couple the heat producing element to a controller, for example. For instance the shell of heating elements 108a, 108b can be made of a material that is highly thermally conductive as well as highly electrically insulative (i.e., having a high dielectric strength). The shell material also may exhibit or provide uniform temperature distribution, a relatively high durability at a low mass, a relatively rapid temperature ramp-up rate, and a low coefficient of thermal expansion. The heating elements may be comprised of one or more transistors, such as power transistors. Optionally, the one or more transistors may provide the only heating source.

Each shell may be made of a ceramic, an alumina ceramic, for example, of high thermal conductivity aluminum nitride (AlN). Another example can be beryllium oxide (BeO), for example, 1 mm thick. The heat producing element (or elements) can be internal, external, or have a portion that is internal and a portion that is external of the highly thermally conductive and highly electrically insulative shell and can be thermally matched to the shell, for example. Thus, optionally, the highly thermally conductive and highly electrically insulative shell may partially or fully enclose the heat producing element.

Heating elements 108a, 108b may be removably attached or fixedly attached to their respective heat spreaders 106. For example, the heating elements 108a, 108b may be fixedly attached to heat spreaders 106 via a thermally resistant epoxy or glue that maintains its bond with the heating element 108a, 108b and heat spreader 106 even at elevated temperatures. Alternatively, a heating element 108a, 108b can be removably attached to a corresponding heat spreader 106 by way of retaining slide grooves, snap-fit, or the like. Embodiments having removably attachable and detachable heating elements 108a, 108b can offer an advantage of being able to switch out heating elements in the case of a defective heating element, or in order to change a size, an output power, a maximum output temperature, and/or an output temperature range of a heating element of the fluid heating apparatus 100.

Each heating element 108a, 108b can have a configuration so as to produce substantially no leakage current or low leakage current, in various embodiments, 10 µA or less, less than 10 µA, 5 µA or less, or 1 µA or less.

The heating elements can be of any suitable shape, size, and/or configuration. Heating elements 108a, 108b can be relatively thin as shown in FIG. 1A and rectangular in the plan view per FIG. 1B, for instance. Each heating element 108a, 108b can have a heating element surface of 10 cm2 and a thickness of 1.6 mm, for example. Moreover, heating elements can be arranged at any suitable position on the heat spreaders 106. FIGS. 1A and 1B, for example, show heating elements 108a, 108b being located on the top and bottom, respectively, of the fluid heating apparatus 100, on their respective heat spreaders 106 and not on or adjacent the fluid channel interface 104. Of course the heating elements can be of any suitable shape, size, and/or configuration and do not have to be elongated, and can be square shape. In various embodiments, heating elements can be formed to take the shape and contour of the heat spreaders to which they are attached.

Temperature sensor 112 can be any suitable sensor to sense a temperature of a heat spreader 106, such as an RTD (Resistance Temperature Detectors) sensor or a thermocouple, for example.

FIG. 1B shows temperature sensor 112 being a plate temperature sensor that is located on top of heat spreader 106. Optionally, another temperature sensor 112 can be arranged on the bottom heat spreader 106. As discussed above, temperature sensor(s) 112 can be electrically coupled to a controller, for example, to provide temperature-related feedback signals to a controller. A controller may use these feedback signals to adjust the output of one or more heating elements, such as heating elements 108a, 108b.

Temperature sensor 112 can be located as shown in FIG. 1B or somewhere else. For example, as another option, a temperature sensor 112 may be located at an input of the fluid heating apparatus 100 and/or a temperature sensor 112 can be located at an output of the fluid heating apparatus 100. In various embodiments, temperature sensor 112 can be located on or adjacent heating elements 108.

Optionally or alternatively, a temperature sensor may be arranged closer to the fluid channel 102 or with a face forming part of the fluid channel 102. In the latter case, the face of the temperature sensor can be non-fouling. Further, temperature sensors may have faces forming part of the fluid channel at the input of the fluid heating apparatus 100 and at the output of the fluid heating apparatus 100. Such a configuration can provide for monitoring of a temperature of the fluid as it enters the heating apparatus 100 and as it is about to exit the fluid heating apparatus 100. Thus, a change in temperature of the fluid as it passes through the fluid heating apparatus 100 can be determined and monitored using feedback signals from the temperature sensors provided to a controller.

FIGS. 1A and 1B show an embodiment of a fluid heating apparatus 100. However, fluid heating apparatuses can be differently configured. FIGS. 2-7 show alternative, non-limiting embodiments.

Figure 2A:
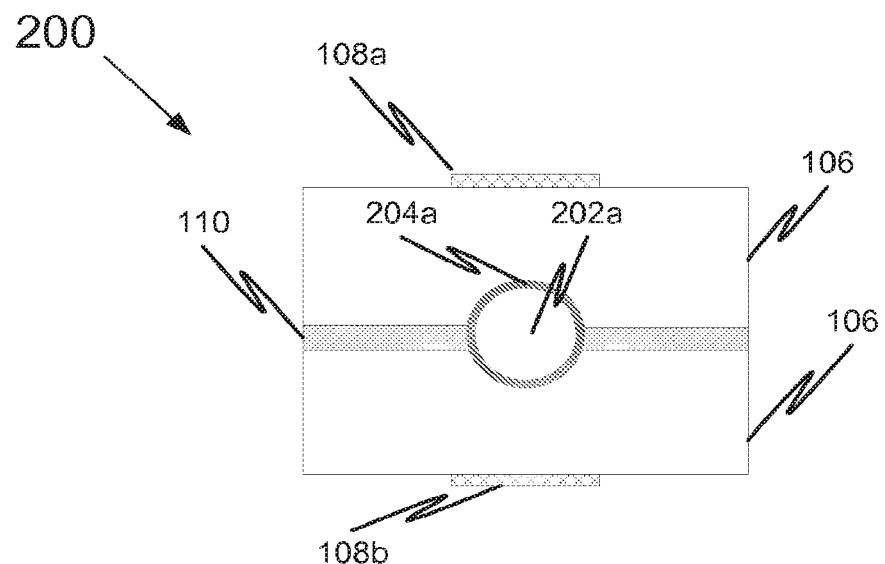
FIG. 2A illustrates a cross section view of another embodiment of a fluid heating apparatus according to the disclosed subject matter.
Figure 2B:
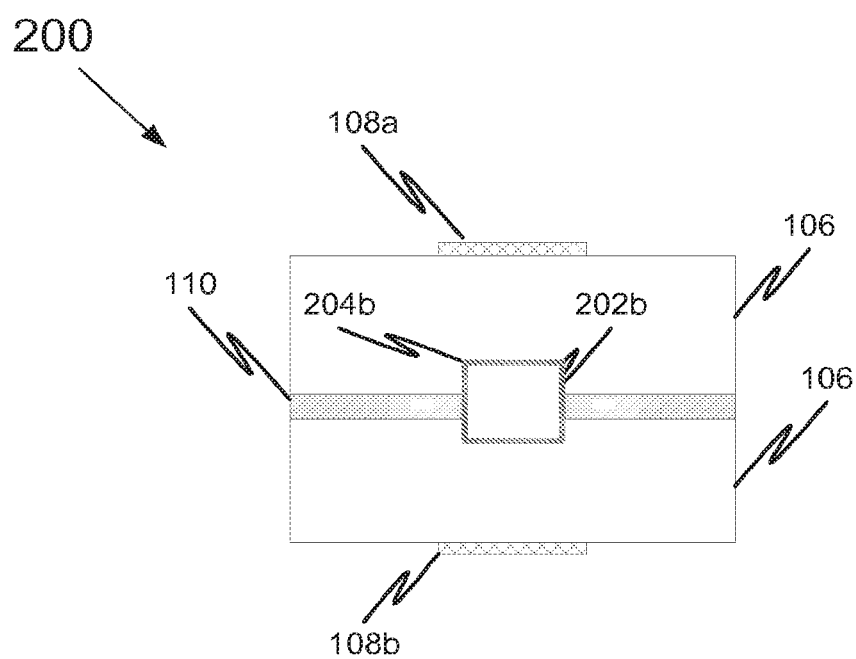
FIG. 2B illustrates a cross section view of a variation of the fluid heating apparatus of FIG. 2A.

FIG. 2A illustrates a cross section view of another embodiment of a fluid heating apparatus 200 according to the disclosed subject matter. FIG. 2B illustrates a cross section view of a variation of the fluid heating apparatus 200. Fluid heating apparatuses 200 shown in FIGS. 2A and 2B are similar to fluid heating apparatus 100 discussed above, but include differently sized and shaped fluid channels and fluid interfaces. FIG. 2A, for example, shows fluid channel 202a and fluid interface 204a being circular in cross section. FIG. 2B on the other hand shows fluid channel 202b and fluid interface 202b being square shaped in cross sectional view. Not explicitly shown, optionally, the circular and square channels can run the entire length of the fluid heating apparatuses 200, or either can run only a portion of the length of the fluid heating channel (e.g., only the middle, only the ends, only one end, etc.). Also note that fluid seal 110 can extend inwardly to "meet" the fluid interfaces 202a, 202b. Alternatively, fluid seal 110 can be omitted and the fluid interfaces 202a, 202b can be enclosed structures that can fully encase the fluid flowing through fluid channels 202a, 202b.

Figure 3A:
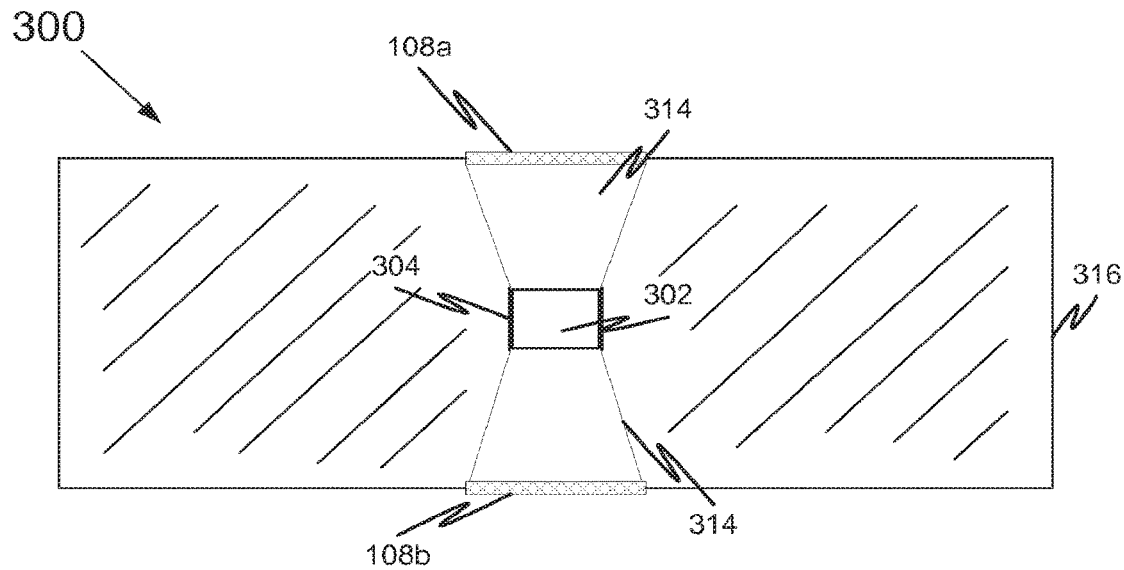
FIG. 3A is an illustration of a cross section view of another embodiment of a fluid heating apparatus according to the disclosed subject matter.
Figure 3B:
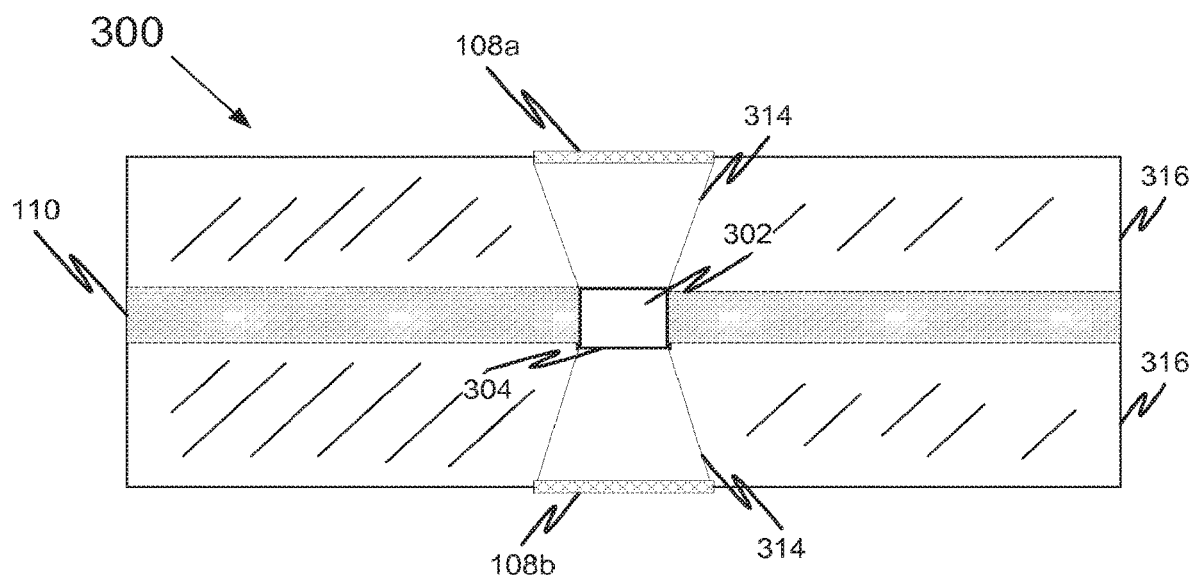
FIG. 3B is an illustration of a cross section view of yet another embodiment of a fluid heating apparatus according to the disclosed subject matter.

FIG. 3A is an illustration of a cross section view of another embodiment of a fluid heating apparatus 300. FIG. 3B shows cross section of a variation of the fluid heating apparatus 300 shown in FIG. 3A.

Fluid heating apparatuses 300 shown in FIGS. 3A and 3B, generally, can incorporate a heat coupling feature, whereby heat from the heating elements 108a, 108b can be coupled via the area of the heating elements to fluid interface 304 and thus to fluid in fluid channel 302 via heat conduction elements 314. Substrate portions 316 in FIGS. 3A and 3B can be heat spreaders as discussed above, or, alternatively, they can be non-heat spreading or conducting components. Substrate portions 316 may be of a different material than heat conduction elements 314. Also, fluid channel 302 and fluid interface 304 are not necessarily square shaped in cross section and can be a non-square rectangle or circular, for example, in cross sectional view. Note also that the heat conduction elements 314 may form to a point or a wedge having a pointed planar surface, for example, at the fluid interface 304.

Figure 4A:
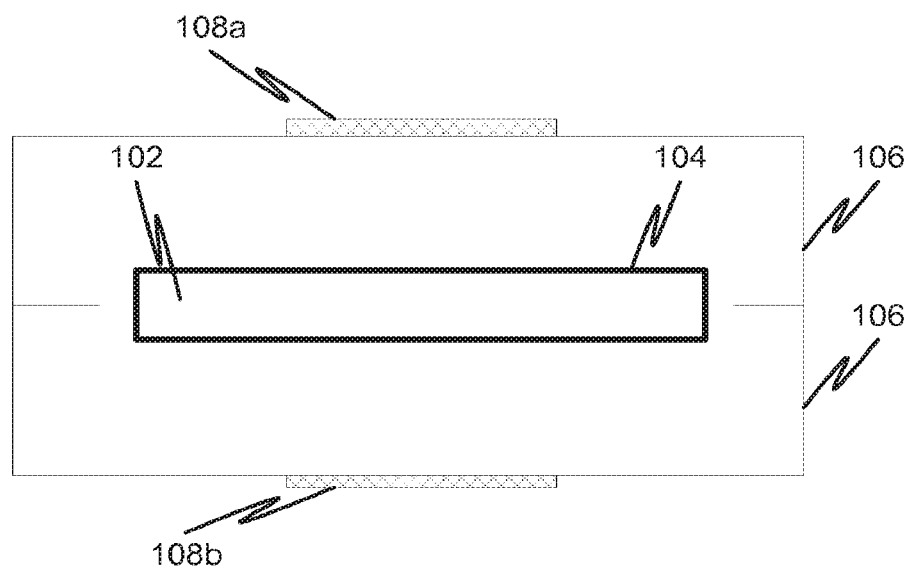
FIG. 4A illustrates a cross section of a fluid heating apparatus according to another embodiment of the disclosed subject matter.

FIG. 4A illustrates a cross section of a fluid heating apparatus according to another embodiment of the disclosed subject matter. The fluid heating apparatus shown in FIG. 4A is similar to fluid heating apparatus 100 shown in FIGS. 1A and 1B, but fluid seal 110 is omitted. Thus, heat spreaders 106 can be coupled directly together to seal the fluid channel 102. Alternatively, fluid interface 104 can completely surround the fluid channel 102.

Figure 4B:
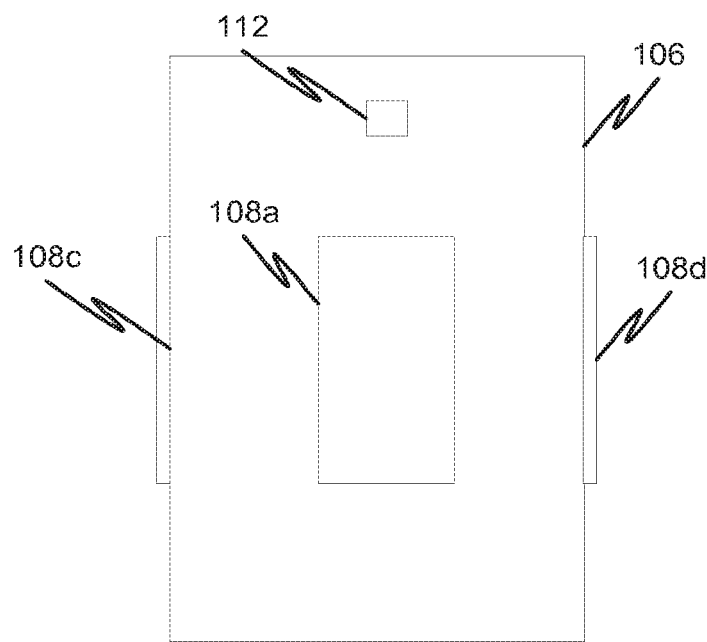
FIG. 4B illustrates an overhead view of a fluid heating apparatus according to another embodiment of the disclosed subject matter.

FIG. 4B illustrates an overhead view of a fluid heating apparatus according to another embodiment of the disclosed subject matter. The fluid heating apparatus of FIG. 4B is similar to fluid heating apparatus 100 shown in FIGS. 1A and 1B, but with side heating elements 108c, 108d (bottom heating element 108b not explicitly shown).

Figure 4C:
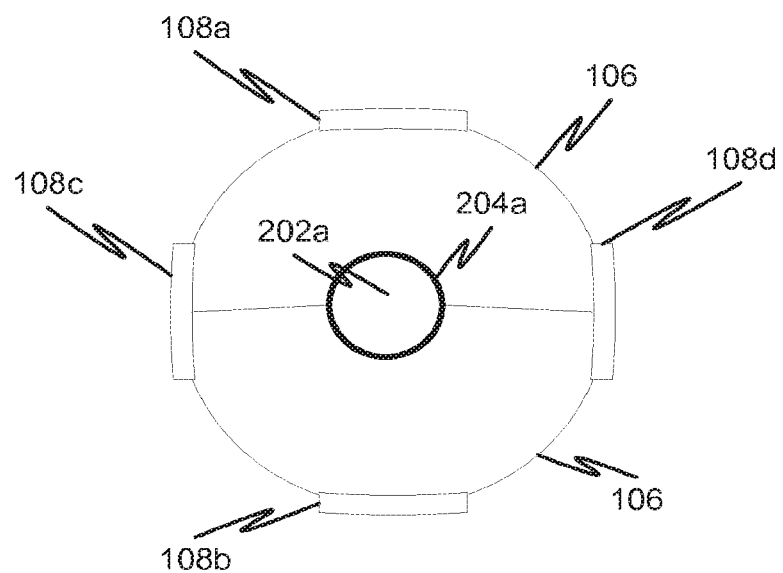
FIG. 4C illustrates a cross section view of a fluid heating apparatus according to another embodiment of the disclosed subject matter.
Figure 4D:
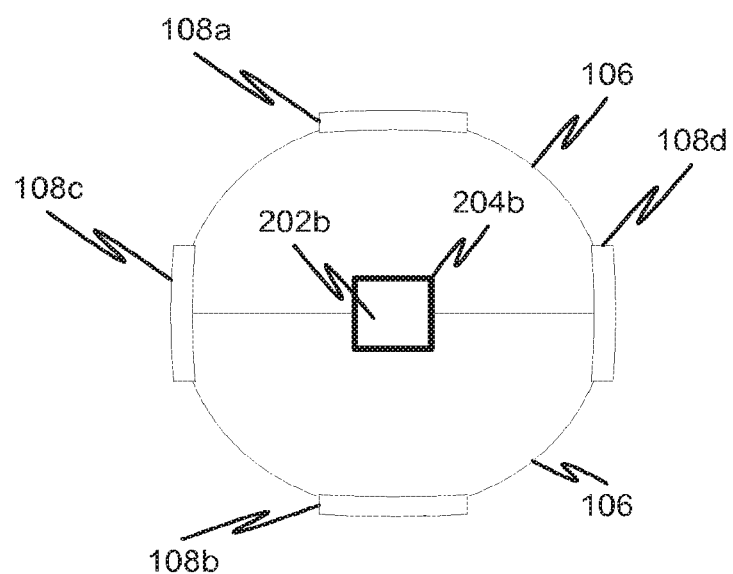
FIG. 4D illustrates a cross section view of a variation of the fluid heating apparatus of FIG. 4C.

FIG. 4C illustrates a cross section view of a fluid heating apparatus according to another embodiment of the disclosed subject matter. FIG. 4D illustrates a cross section view of a variation of the fluid heating apparatus of FIG. 4C. The fluid heating apparatuses of FIGS. 4C and 4D have circular cross sections, with four heating elements 108a, 108b, 108c, 108d spaced equidistance from adjacent heating elements on the outside of the fluid heating apparatus body. The heating elements can be flat plates or they can be shaped based on the shape of the fluid heating apparatus body. For example, the heating elements 108a, 108b, 108c, 108d may have a curvature based on the radius of curvature of the fluid heating apparatus body. Optionally, the entire heating element may have a curvature based on the curvature of the fluid heating apparatus. Alternatively, only one side—the side coupled to the fluid heating apparatus body—may be curved.

In alternative embodiments FIGS. 4A, 4B, 4C, and 4D, there may only be one heat spreader 106 that completely surrounds the fluid channel 102/202 (i.e., the heat spreader is formed in one piece with the fluid channel formed therein).

Figure 5A:
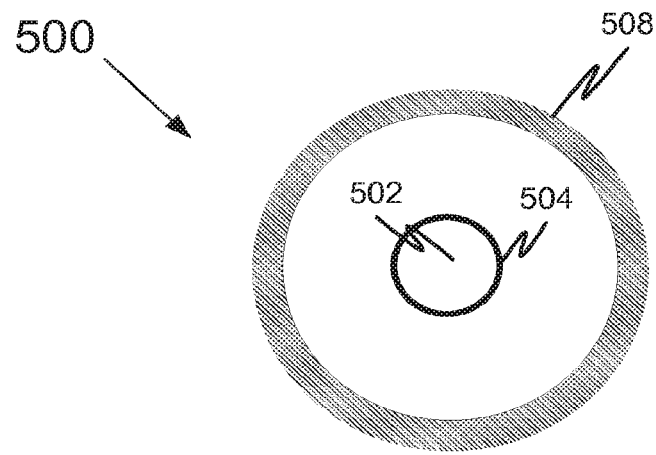
FIG. 5A illustrates a cross section view of yet another embodiment of a fluid heating apparatus according to the disclosed subject matter.
Figure 5B:
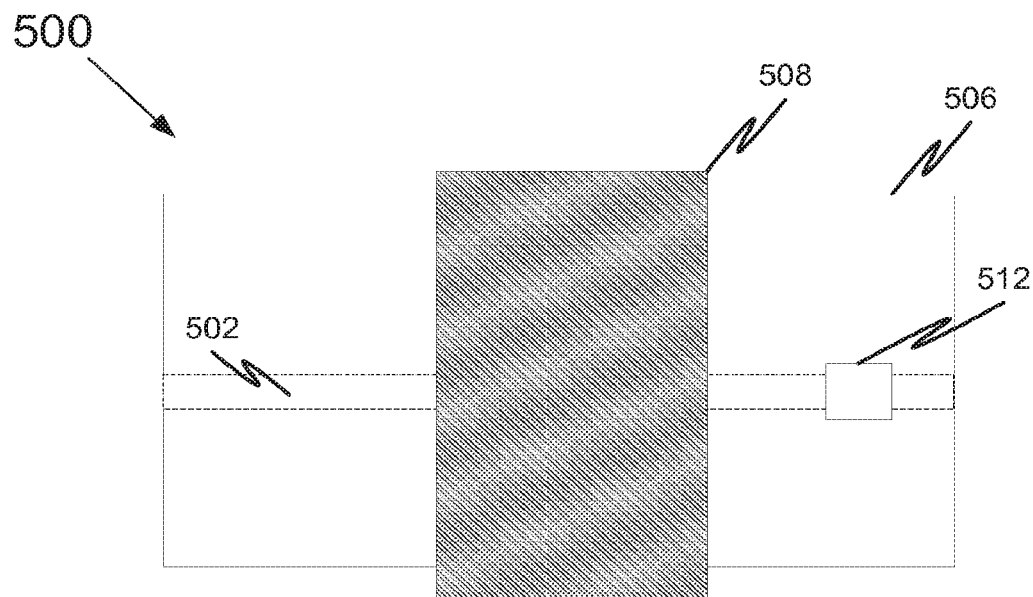
FIG. 5B illustrates a side view of the fluid heater according to FIG. 7A.

FIG. 5A illustrates a cross section view of yet another embodiment of a fluid heating apparatus 500 according to the disclosed subject matter. FIG. 5B illustrates a side view of the fluid heater 500. As can be seen, fluid heating apparatus 500 includes one heating element 508 surrounding in a radially inward direction a portion of the fluid heating apparatus 500. The fluid channel 502 (shown as dashed lines in FIG. 5B) is surrounded by fluid interface 504, which is surrounded by heat spreader 506, which in turn has a portion surrounded by heating element 508. The portion of the heating element 508 which surrounds heat spreader 506 can be the portion shown in FIG. 5A, another portion of same size, or the entire portion of the heat spreader 506, for example. Fluid heating apparatus 500 also can have a temperature sensor 512. Heating element 508 can be positioned closer to the input of the fluid heating apparatus 500, or it can be positioned closer to the output of the fluid heating apparatus 500. FIG. 5B, for example, shows the heating element 508 being positioned an equal distance from the input and output of the fluid heating apparatus 500. Moreover, optionally, in various embodiments, heating element 508 may be slidable or movable along the length of the fluid heating apparatus 500 such that it can be repositioned. Locking devices, such as detents, hooks, etc. may be provided to hold the heating element 508 in desired position.

FIGS. 6A-6D show channel configurations for heating apparatuses according to embodiments of the disclosed subject matter. Note that for FIGS. 6A-6D, additional heating apparatus components, such as heating element(s), temperature sensor(s), fluid interface(s), etc., are not shown.

Figure 6A:
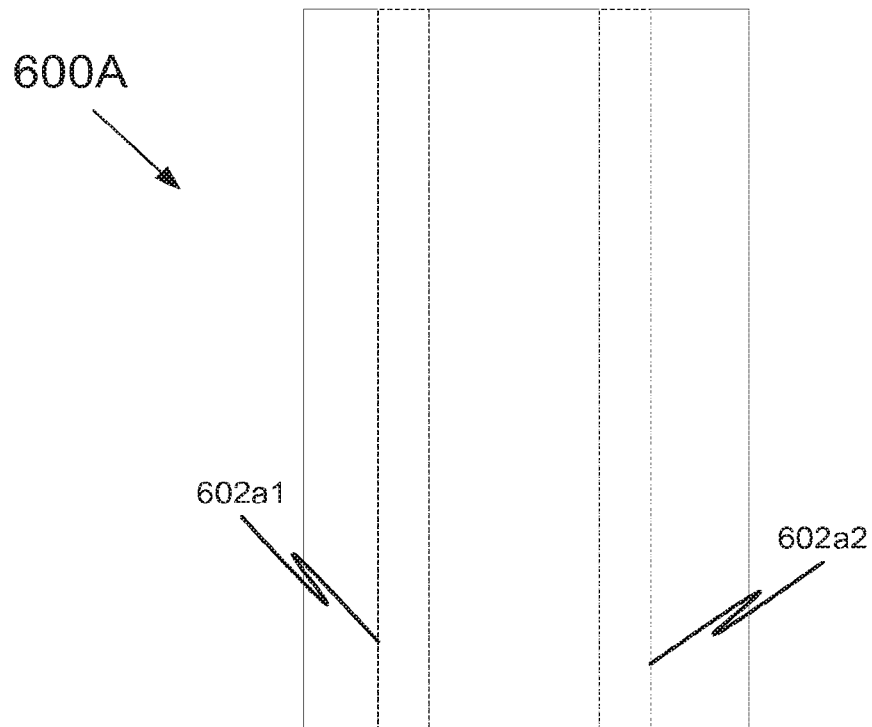
FIG. 6A is an overhead view of a side-by-side multi-channel fluid heating apparatus according to embodiments of the disclosed subject matter.
Figure 6B:
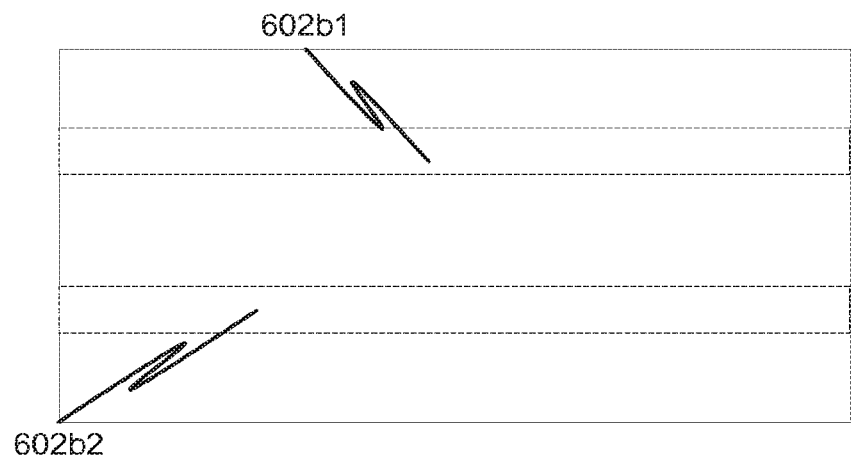
FIG. 6B is a side view of an over/under multi-channel fluid heating apparatus according to embodiments of the disclosed subject matter.

FIG. 6A is an overhead view of a side-by-side multichannel fluid heating apparatus 600A according to embodiments of the disclosed subject matter. Fluid channels 602a1, 602a2, shown by dashed lines, are positioned side-by-side in overhead view. Optionally, they may be at a same level in side view. FIG. 6B is a side view of an over/under multichannel fluid heating apparatus 600B according to embodiments of the disclosed subject matter. Fluid channel 602b1 is shown as being positioned above fluid channel 602b2. Optionally, fluid channels 602b1, 602b2 can be directly above/below one another in overhead view.

Figure 6C:
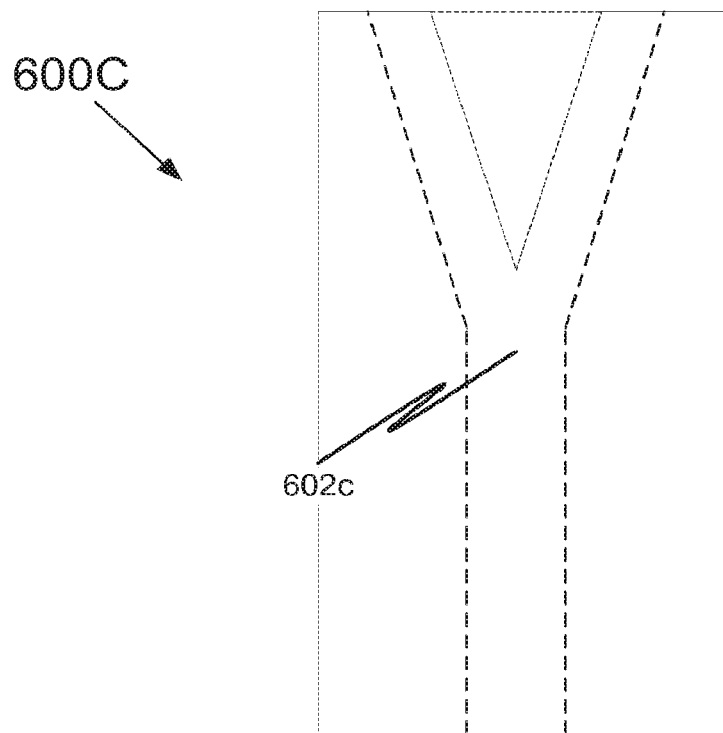
FIG. 6C is an illustration of an overhead view of a fluid heating apparatus with a channel having a bifurcated portion according to embodiments of the disclosed subject matter.
Figure 6D:
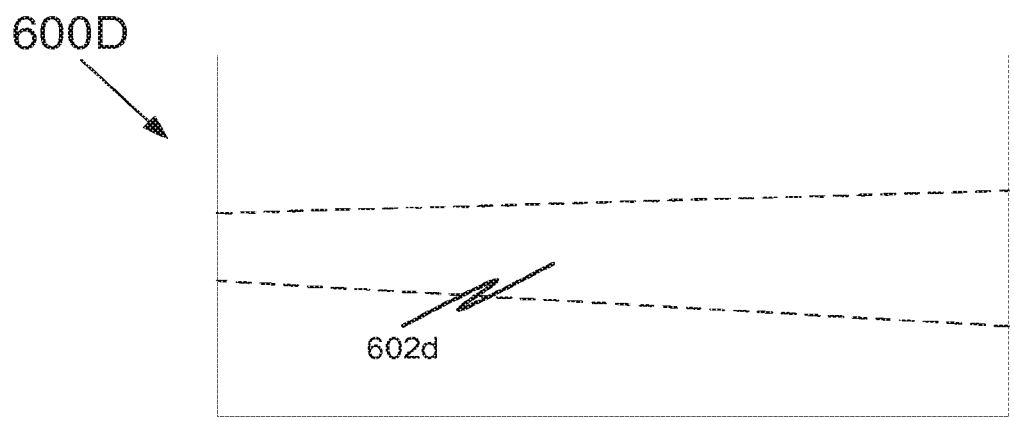
FIG. 6D is a side view of a fluid heating apparatus having a non-uniform fluid channel.

FIG. 6C is an illustration of an overhead view of a fluid heating apparatus 600C with a fluid channel 602c having a bifurcated portion according to embodiments of the disclosed subject matter. The bifurcated portion can be at the input and/or output side of the fluid heating apparatus 600C. FIG. 6D is a side view of a fluid heating apparatus 600D having a fluid channel 602d with a non-uniform flow path. The fluid path can increase or decrease from the input side of the fluid heating apparatus 600D.

In the embodiments discussed herein, a number of different fluid channels have been described and shown. However, fluid channels are not limited to those described above, and can take other configurations. In various embodiments, the interior of the fluid channel can be smooth. Alternatively, some or all of the interior can be irregular, for example grooved, threaded, corkscrew, ridged, etc. Optionally, the configuration of the fluid channel can optimize fluid flow, for instance, to create a vortex. Other channel configurations can also be implemented, such as a looping system comprised of one or more channel loops arranged generally horizontally. Additionally, the fluid channel can have formed or arranged therein or at inputs or outputs thereof, one or more filter elements to filter the fluid flowing through the fluid channel.

Figure 7A:
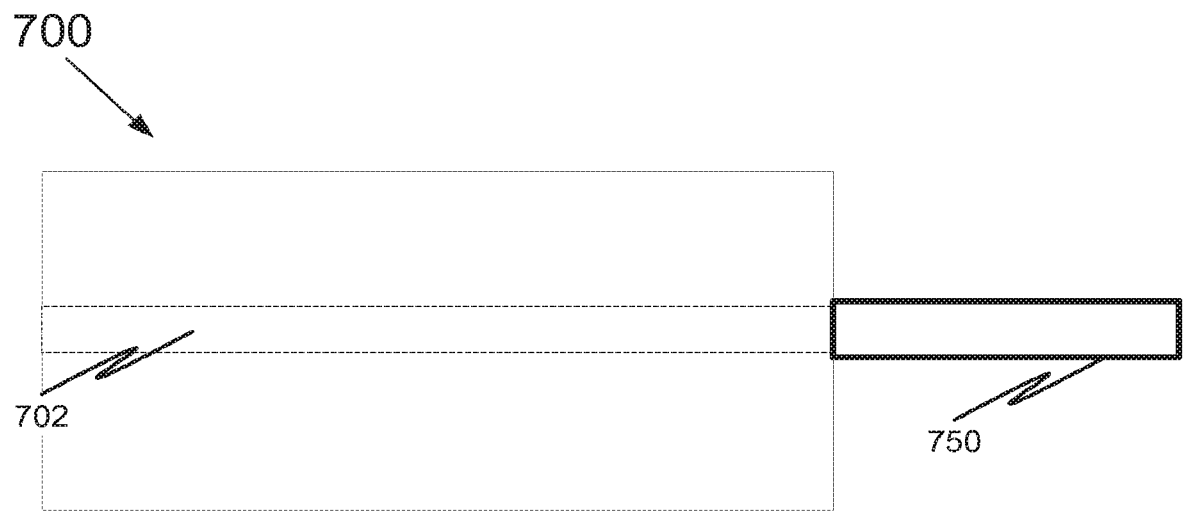
FIG. 7A illustrates a side view of a fluid heating apparatus with an attachment according to embodiments of the disclosed subject matter.
Figure 7B:
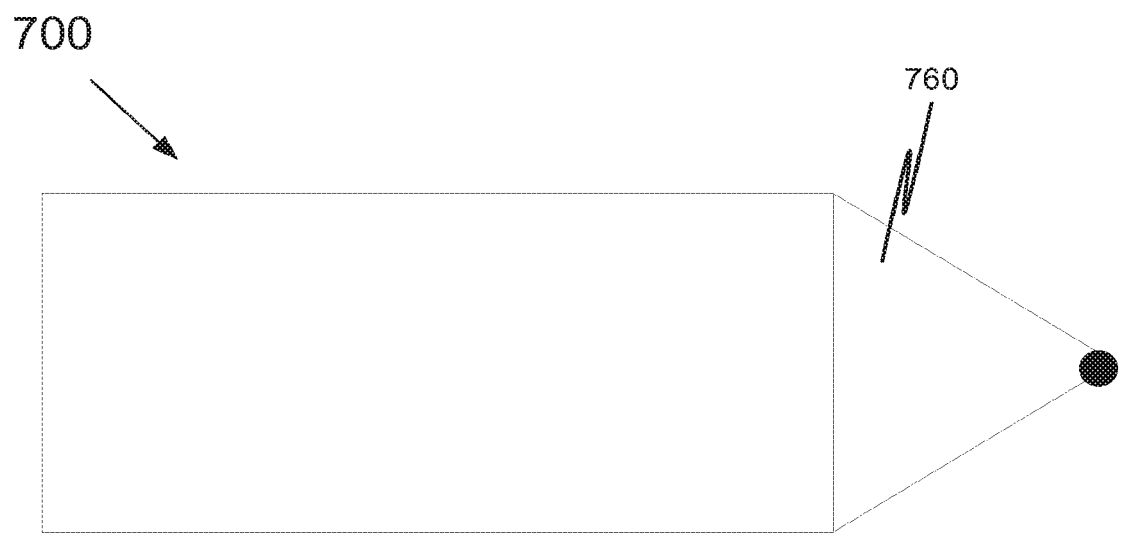
FIG. 7B illustrates a side view of the fluid heating apparatus of FIG. 5A with another attachment according to embodiments of the disclosed subject matter.

Fluid heating apparatuses according to embodiments of the disclosed subject matter can have ends thereof coupled to any suitable attachment. For example, FIG. 7A shows a fluid heating apparatus 700 with an attachment 750 in the form of tubing (e.g., miniature polymeric tubing) coupled to fluid heating apparatus 700 in alignment with fluid channel 702. Attachment 750 can be attached to the input of the fluid heating apparatus 700, the output of the fluid heating apparatus 700, or both. FIG. 7B shows fluid heating apparatus 700 with another attachment 760 in the form of a syringe. Thus, the fluid heating apparatus 700 shown in FIG. 7B can be implemented as a syringe heater. Leak detectors can also be implemented at the input(s) and/or output(s) of fluid heating apparatuses according to embodiments of the disclosed subject matter. Such leak detectors can be used to detect leaks at interfaces between the fluid heating apparatus and attachments. Note that for FIGS. 7A and 7B, additional heating apparatus components, such as heating element(s), temperature sensor(s), fluid interface(s), etc. are not shown.

In the embodiments discussed herein, a number of fluid heating apparatuses have been described and shown. However, fluid heating apparatuses are not limited to those described above, and can take any suitable configuration. In various embodiments, fluid heating apparatuses may include a window or windows to view fluid levels and/or to monitor for air bubbles. Various embodiments also may employ a bubble trap.

Figure 8:
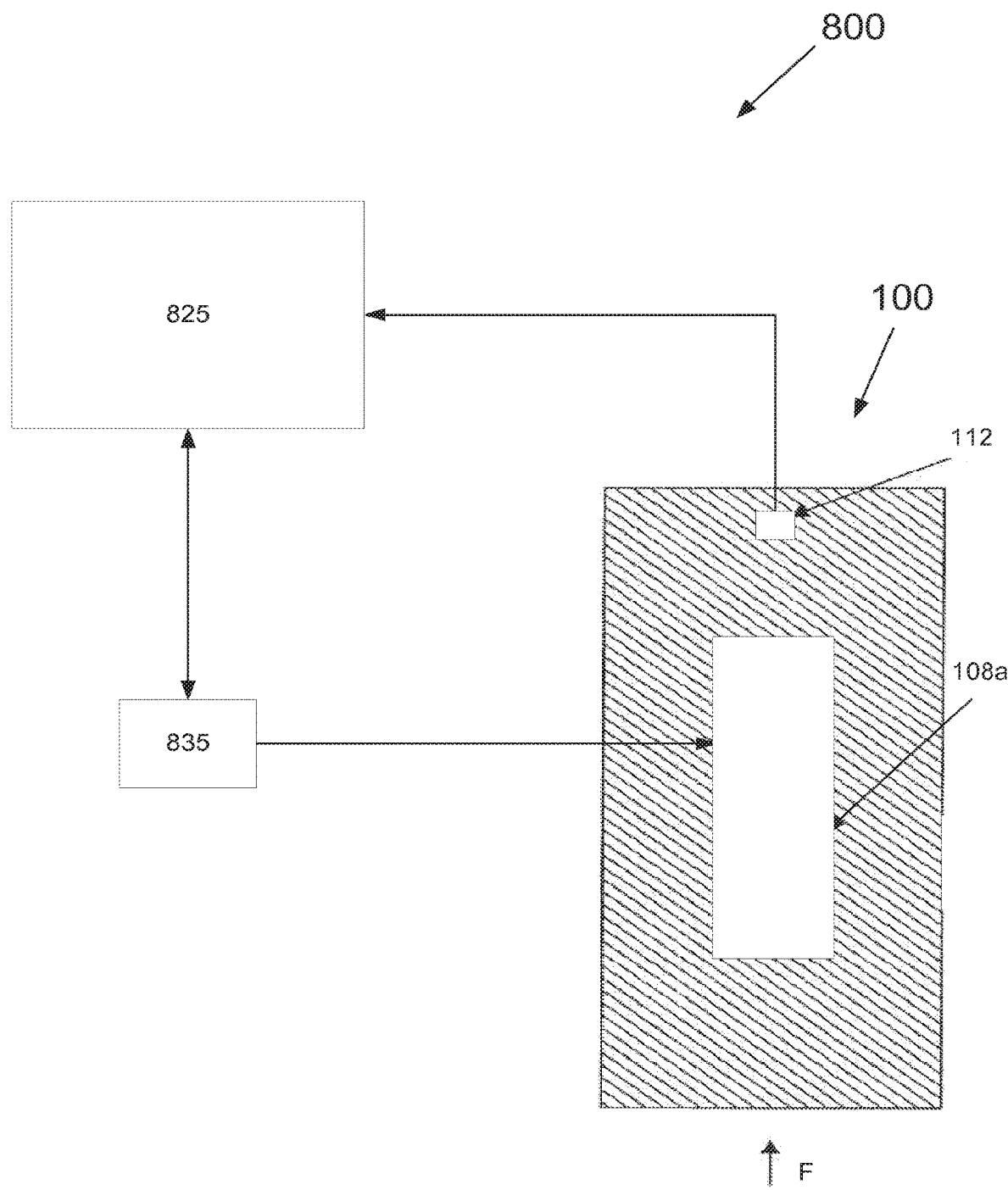
FIG. 8 shows a system having the fluid heating apparatus of FIGS. 1A and 1B as a component according to embodiments of the disclosed subject matter.

FIG. 8 shows a system 800 having the fluid heating apparatus of FIGS. 1A and 1B. Not shown in FIG. 8 are the fluid connections into and out of fluid heating apparatus 100. System 800 can be used with any suitable medical equipment, such as a dialysis system.

System 800 can include fluid heating apparatus 100, a controller 825, and a driver 835. As shown in FIG. 8, fluid heating apparatus 100 is electrically coupled to controller 825 and driver 835. More specifically, controller 825 is electrically coupled to temperature sensor 112 and can receive feedback signals from temperature sensor 112, such as temperature-related feedback signals. In the case of an embodiment where multiple temperature sensors are implemented, controller 825 can be coupled to each temperature sensor to receive individual temperature sensor signals.

Controller 825 is coupled to driver 835 and can provide control signals to driver 835, for example, in response to feedback signals from temperature sensor 112. Control signals provided by the controller 825 to driver 835 may be to control operation of the heating element(s) 108, such as on/off operation, the amount of heat output by the heating element(s), ramp up heating time, applied current, to promote unity power factor, to balance transistor power, to control current to make constant the power as the line voltage varies, etc.

Controller 825 also may provide control signals to driver 835 by measuring measure RMS voltage during a half cycle of the line and setting the command ratio for the next cycle. A PWM output by controller 825 may be used for generating a multiplication factor. Any of the foregoing control can be used to accurately set a temperature of a heating element to a predetermined temperature (or within a predetermined temperature range) and maintain the heating element at such temperature (or within the temperature range).

Not shown in FIG. 8, controller 825 may be coupled to another "master" controller as part of an overall fluid processing system. Additionally, in various embodiments, controller 825 may be located on-board the fluid heating apparatus 100, or, alternatively, it can be located remotely from fluid heating apparatus 100 and coupled thereto via electrical connections. Optionally, only driver 835 may be located on-board fluid heating apparatus 100.

Additionally, controller 825 or a fluid processing system according to embodiments of the disclosed subject matter, can monitor in real-time temperature of a fluid flowing through a fluid channel of a fluid heating apparatus and set a temperature of the a fluid heating apparatus in order to heat the fluid flowing through the fluid channel to a predetermined temperature. Controller 825 or a fluid processing system according to embodiments of the disclosed subject matter can also determine whether electricity is supplied to any of its components, such as controller 825, heating element 108, etc. Controller 825 or a fluid processing system according to embodiments of the disclosed subject matter can also determine whether fluid is present or flowing through the fluid heating apparatus 100 (e.g., infrared detection) and/or can generate an alarm in response to monitoring of temperature (e.g., a low temperature alarm and/or a high temperature alarm). Controller 825 may turn off heating elements 108 or cause output thereof to be reduced if it is determined that a temperature of the element and/or the fluid is above a predetermined upper threshold.

FIGS. 9A-9E illustrate examples of circuitry that can be used as part or all of driver 835 to control fluid heating apparatuses according to embodiments of the disclosed subject matter. FIG. 9F shows a current command signal output of the circuitry of FIG. 9E. Generally speaking, the control circuitry shown in FIGS. 9A-9E can operate under linear controlled resistance control. Further, circuitry according to embodiments of the invention can implement solid state devices such as solid state power regulators (e.g., transistors, such as MOSFETs, IGBTs, BJTs, or combinations thereof).

Figure 9A:
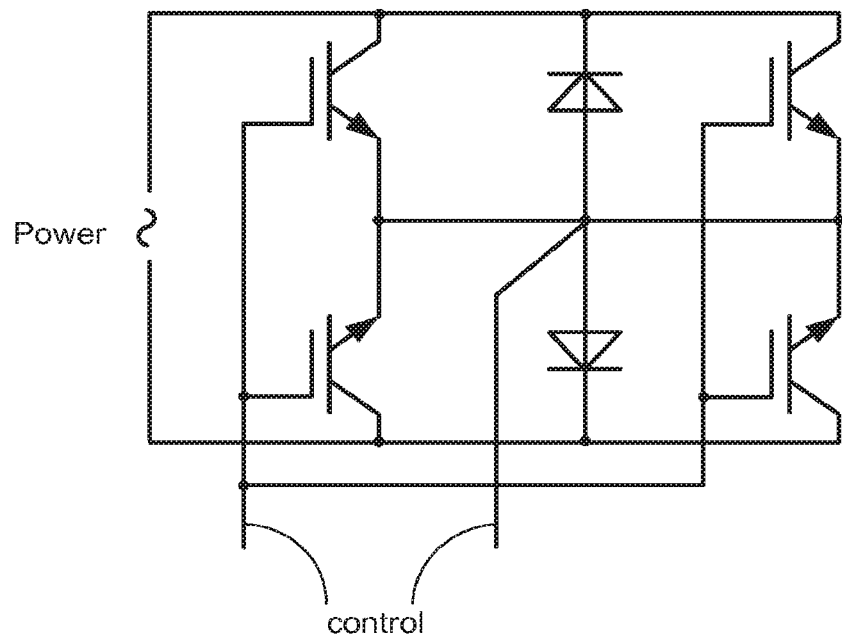
FIGS. 9A-9E illustrate examples of control circuitry to control fluid heating apparatuses according to embodiments of the disclosed subject matter.
Figure 9B:
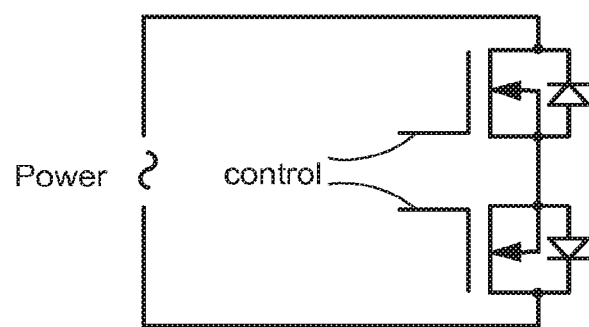
Figure 9C:
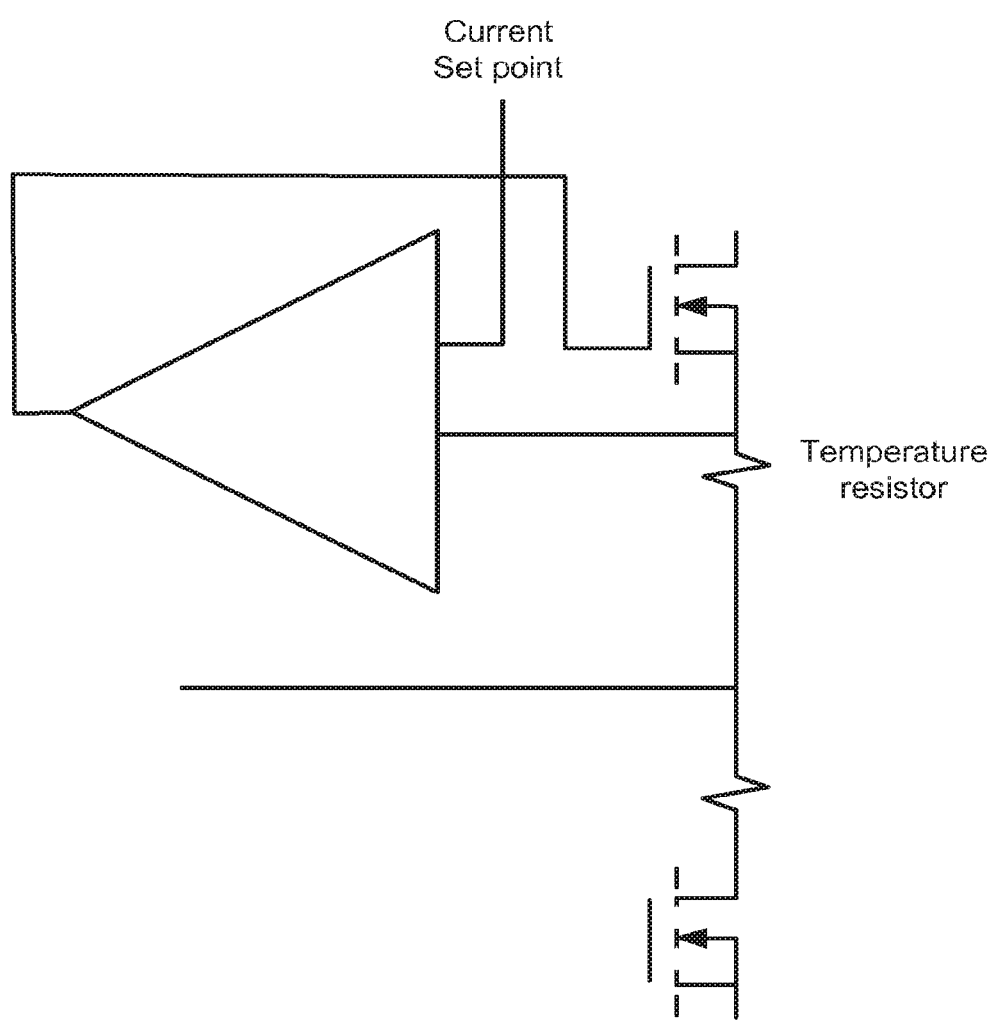
Figure 9D:
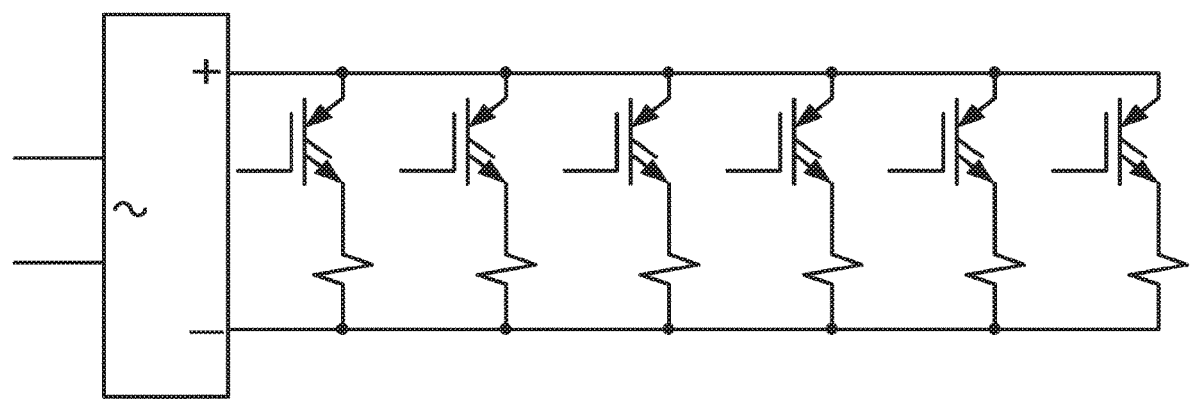

FIGS. 9A and 9B show driver circuitry using IGBTs and MOSFETs, respectively, as dissipative elements. Each transistor may be controlled, for example, to conduct for an AC half cycle. FIG. 9C is circuitry for a current control signal. The circuitry in FIG. 9C for current control signal can be designed and operative such that the current is proportional to a line AC voltage for unity power factor, for instance.

In various embodiments, the AC input voltage may be rectified with a bridge and the transistors can dissipate for each half cycle. See, for example, FIG. 9D. The emitter resistors can be used to balance the current between the IGBTs when the design is implemented with the gates connected in parallel, for example. Alternately, operation amplifiers (e.g., six op-amps) can be used to drive each gate, independently closing the loop on current sensing for the associated emitter resistor. Each collector can be fused in case there is a failure.

Figure 9E:
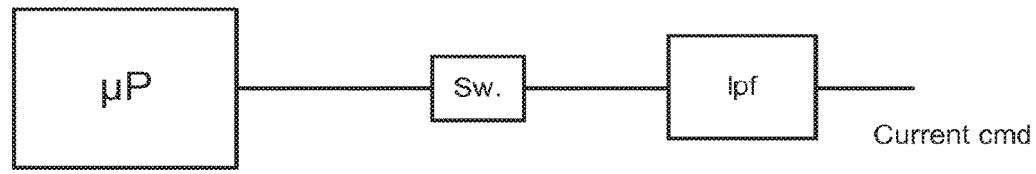
Figure 9F:
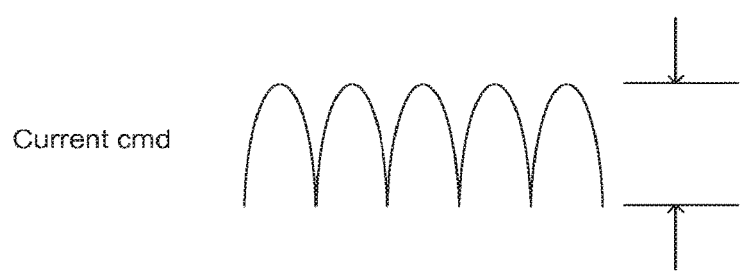
FIG. 9F shows a current command signal output of the circuitry of FIG. 9E.

In various embodiments, a current command for a load may be proportional to the AC voltage in order to get unity power factor. Yet as the line voltage fluctuates the load current can be controlled as 1/AC VRMS to keep power constant. In various embodiments, processor uP can provide this control function. Processor uP can measure the RMS voltage during a half cycle of the line voltage and set a command ratio for the next cycle. A PWM signal could be used for generating the multiplication factor. Thus, in various embodiments, processor uP may control PWM signals to provide a dissipated power per the command it receives from a master controller. This power can be held constant as the line voltage varies or is caused to vary. Alternatively, processor uP may provide the command to another controller, such as another microprocessor or controller 825. See FIGS. 9D-9F, for example. FIG. 9E, for example, shows processor uP outputting an output PWM signal to a switch to produce a rectified line voltage signal, which can be passed through a low pass filter, for instance, to produce a current command as indicated above. FIG. 9F shows an example of a rectified current command having an amplitude proportional to the PWM duty cycle.

Figure 10A:
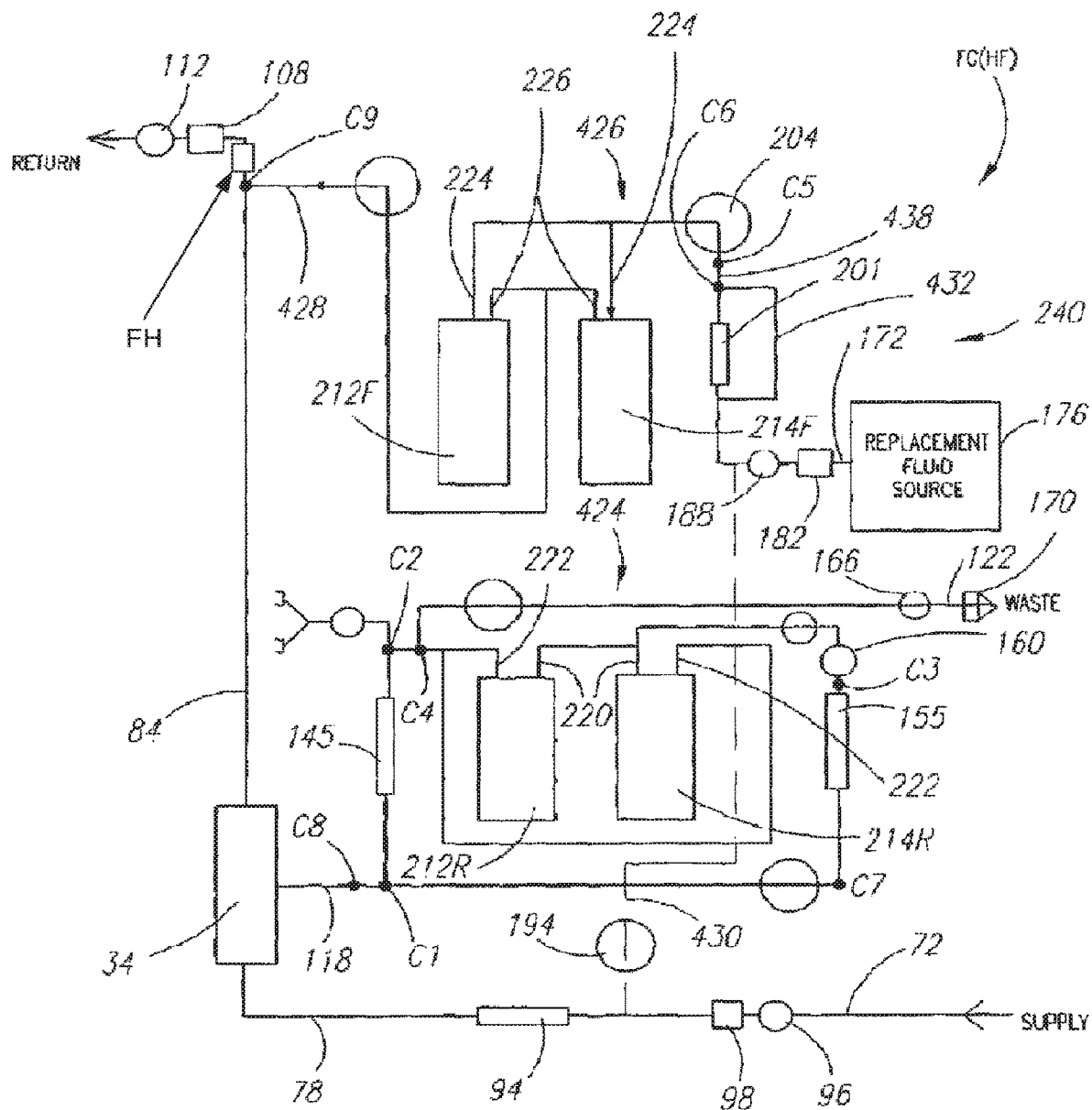
FIG. 10A illustrates embodiments of the disclosed subject matter.
Figure 10B:
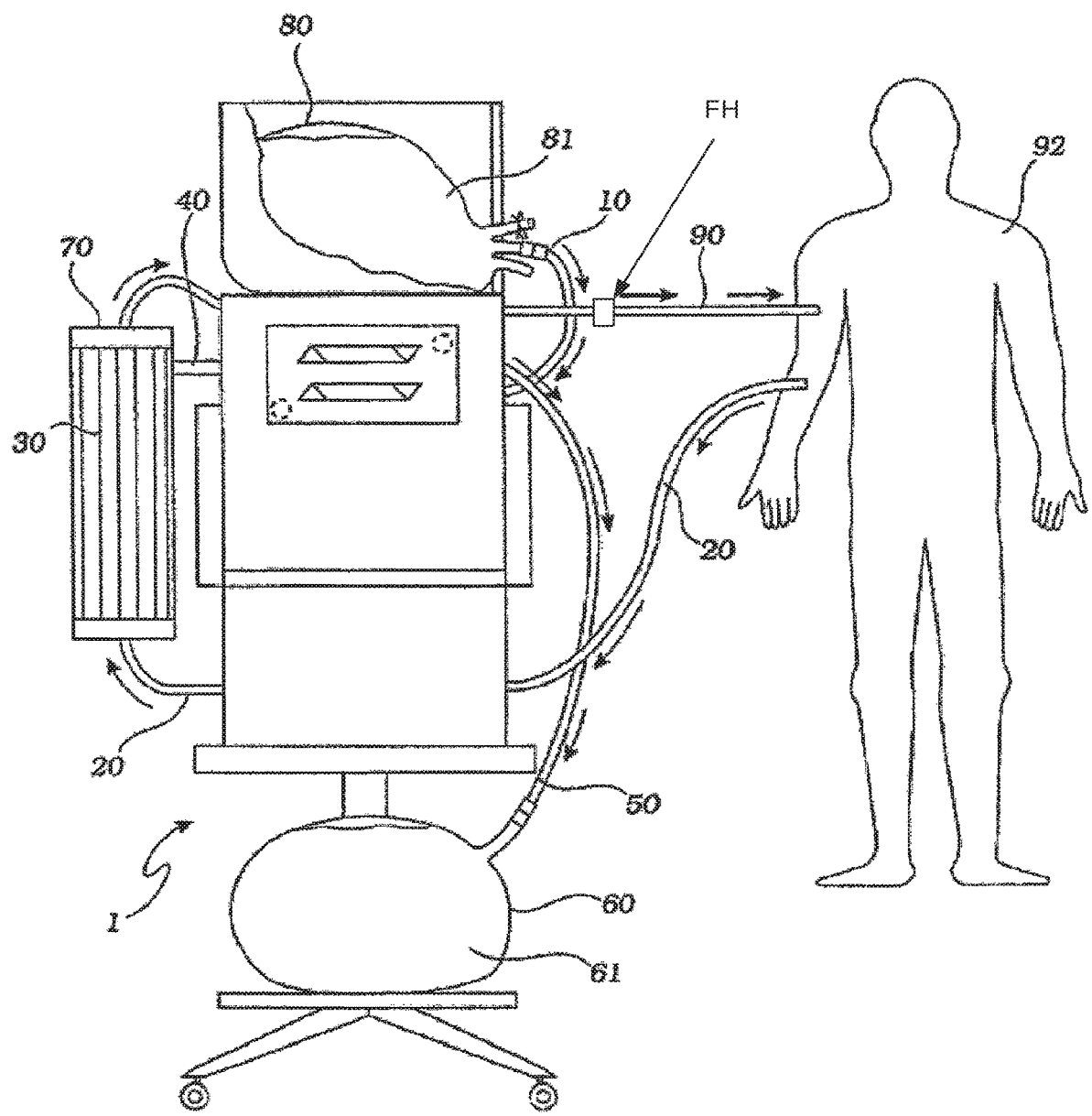
FIG. 10B illustrates embodiments of the disclosed subject matter.

FIGS. 10A and 10B systems in which fluid heating apparatuses according to embodiments of the disclosed subject matter may be incorporated.

Figure 12:
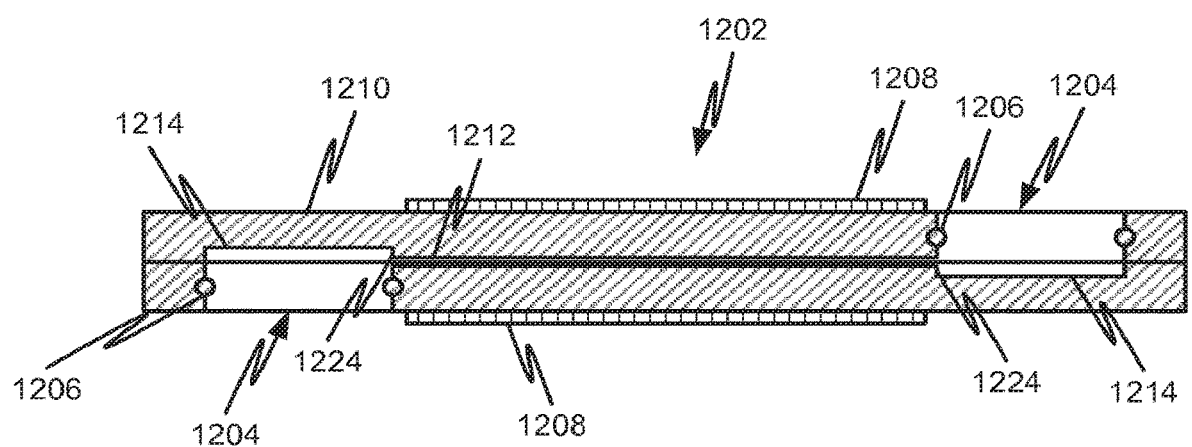
FIG. 12 is a heating apparatus according to another embodiment of the invention.

FIG. 10A shows FIG. 12 from U.S. Pat. No. 7,780,619 issued Aug. 24, 2010 modified to incorporate fluid heating apparatus FH according to embodiments of the disclosed subject matter. The entire content of U.S. Pat. No. 7,780,619 is hereby incorporated by reference in its entirety into the present application. Fluid heating apparatus FH can be located as shown in FIG. 10A, or it can be positioned at any suitable location, either inside or outside of an enclosure of the blood processing apparatus in U.S. Pat. No. 7,780,619. Multiple fluid heating apparatuses FH also may be employed, for instance, in series in a patient line.

FIG. 10B shows FIG. 1 from U.S. Pat. No. 7,419,597 issued Sep. 2, 2008 modified to incorporate fluid heating apparatus FH according to embodiments of the disclosed subject matter. The entire content of U.S. Pat. No. 7,419,597 is hereby incorporated by reference in its entirety into the present application. Fluid heating apparatus FH can be located as shown in FIG. 10B, or it can be positioned at any suitable location, such as inside hemofiltration device 1 in U.S. Pat. No. 7,419,597. Further, multiple fluid heating apparatuses FH also may be employed, for instance, in series in the patient line 90. Optionally, a heating plate may be employed under bag 81 in FIG. 10B, for example. Optionally, the heating plate can be significantly smaller in area than the overall surface on which the bag 81 rests.

Accordingly, fluid heating apparatuses according to embodiments of the disclosed subject matter can be used with or as a component of any suitable fluid processing systems or devices, such as those indicated above regarding FIGS. 10A and 10B.

Figure 11:
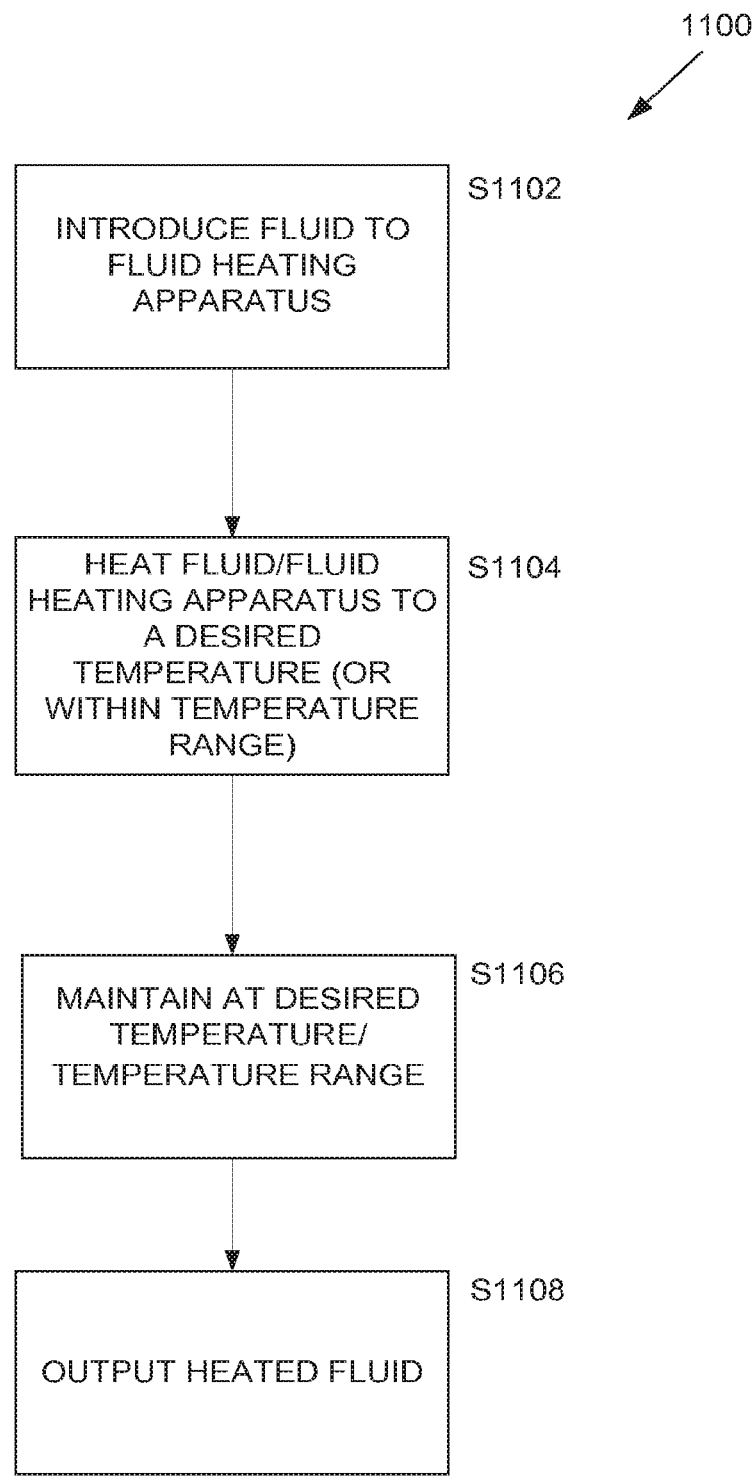
FIG. 11 illustrates a method according to embodiments of the disclosed subject matter.

FIG. 11 illustrates a method 1100 according to embodiments of the disclosed subject matter.

Fluid may be introduced to a fluid heating apparatus as described herein S1102. The fluid can be heated using the fluid heating apparatus as described herein S1104. In various embodiments a controller can provide control signals to a heating element so that the heating element is heated to a desired temperature in order to heat the fluid to a desired temperature. The temperature of the fluid and/or the fluid heating apparatus can be monitored, for example, via a temperature sensor or sensors located on the fluid heating apparatus, to maintain the temperature at the desired temperature or within the desired temperature range 51106. If the temperature of the fluid or the fluid heating apparatus is not at a desired temperature (or within a desired temperature range), the method can provide control signals to adjust the temperature so that it is at the desired temperature or within the desired temperature range. Fluid may be output from the fluid heating apparatus at the desired temperature or within the desired temperature range 51108.

FIG. 12 shows an embodiment of a heater device 1202 with ports 1204 and a channel 1212 formed by machining suitable recesses in metal plates 1210. Each port has a blind end recess 1214 that is deeper than the channel which can facilitate uniform distribution of flow in the channel inlet 1224. Incidentally, either end may be used as in inlet in the present embodiment although only one blind end recess 1214 may be provided in alternative embodiments. A ceramic insulator 1208, as in other embodiments, can provide for high thermal contact, high electrical (including capacitive coupling) isolation of the heating elements (e.g., transistors; not shown but as describe elsewhere). The metal plates may be of copper or other highly thermally conductive material.

The heating elements may be urged by resilient urging members to accommodate differential thermal expansion according to known methods and devices, such as springs. As in any of the present embodiments, thermal paste may be used to ensure high thermal contact between layered components. The internal channel 1212 may be defined by recesses milled into the plates 1210. The internal surfaces may be plated for biocompatibility. For example, copper plates may be plated with nickel then gold. O-rings 1206 may be used to provide high pressure seal to tubular channels. The sandwich structure of the heating device 1202 may be held together using a single compression device, bonded by suitable means or other fasteners may be used. This assembly structure may be applied to any of the embodiments described herein. The entire assembly, and any other embodiments described herein, may be potted in a resilient material such as RTV.

Although particular configurations have been discussed herein, other configurations can also be employed. It is, thus, apparent that there is provided, in accordance with the present disclosure, fluid heating devices, systems, and methods. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicant intends to embrace all such alternatives, modifications, equivalents, and variations that are within the spirit and scope of the present invention.

The invention claimed is:

1. A fluid heating device for medical fluids, comprising:
    an assembly of flat plates held in parallel relation, at least one of the flat plates having a recess in a surface facing another of the flat plates, thereby forming a channel; and
    at least one semiconductor power controller respectively in contact with the at least one of the flat plates and serving as a lone heating source and arranged to respectively convey a majority of heat dissipated thereby conductively into the at least one of the flat plates, wherein
    the at least one of the flat plates has at least two openings in fluid communication with the channel and has sealing elements adapted for attachment to external fluid tubing, and
    the channel extends in a straight path between the at least two openings, and
    wherein at least one of the at least two openings extends entirely through the at least one of the flat plates from the surface facing the other of the flat plates to an opposite surface at a major face of the at least one of the flat plates.

2. The fluid heating device of claim 1, wherein the semiconductor power controller includes a transistor.

3. The fluid heating device of claim 1, wherein the semiconductor power controller includes multiple transistors.

4. The fluid heating device of claim 1, wherein the flat plates are of copper, at least a surface of which is coated with a biocompatible material.

5. The fluid heating device of claim 1, wherein the channel has an aspect ratio of more than ten to one.

6. The fluid heating device of claim 1, wherein the channel has a depth dimension perpendicular to a metal plate major face that is less than 5 mm.

7. The fluid heating device of claim 1, wherein the channel has a depth dimension perpendicular to a metal plate major face that is less than 2 mm.

8. The fluid heating device of claim 1, wherein the channel has a depth dimension perpendicular to a metal plate major face that is less than 1 mm.

9. The fluid heating device of claim 1, further comprising an electrical insulator between the semiconductor power controller and the at least one of the flat plates.

10. The fluid heating device of claim 1, wherein one of the sealing elements is disposed in the at least one of the at least two openings.

11. A fluid heating device for medical fluids, comprising:
    an assembly of flat plates held in parallel relation, at least one of the flat plates having a recess in a surface facing another of the flat plates, thereby forming a channel; and
    at least one semiconductor power controller respectively in contact with the at least one of the flat plates and serving as a lone heating source and arranged to respectively convey a majority of heat dissipated thereby conductively into the at least one of the flat plates, wherein
    the at least one of the flat plates has at least two openings in fluid communication with the channel and has sealing elements adapted for attachment to external fluid tubing,
    the channel extends in a straight path between the at least two openings,
    wherein one of the at least two openings is a first blind end recess in the surface facing the other of the flat plates, and
    wherein another one of the at least two openings is a first hole extending entirely through the at least one of the flat plates from the surface facing the other of the flat plates to an opposite surface at a major face of the at least one of the flat plates.

12. The fluid heating device of claim 11, wherein one of the sealing elements is disposed in the first hole.

13. The fluid heating device of claim 11, wherein the other of the flat plates has a second blind end recess in a surface facing the at least one of the flat plates, and a second hole extending entirely through the other of the flat plates from the surface facing the at least one of the flat plates to an opposite surface at a major face of the other of the flat plates, and wherein the second blind end recess interfaces with the first hole and the second hole interfaces with the first blind end recess.

14. The fluid heating device of claim 13, wherein one of the sealing elements is disposed in the first hole and another one of the sealing elements is disposed in the second hole.

* * * * *